United States Patent
Falkenstein et al.

(10) Patent No.: US 10,590,186 B2
(45) Date of Patent: *Mar. 17, 2020

(54) IMMUNOGLOBULIN PURIFICATION

(71) Applicant: HOFFMANN-LA ROCHE INC., Little Falls, NJ (US)

(72) Inventors: Roberto Falkenstein, Munich (DE); Claudia Giessel, Bad Toelz (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 120 days.

This patent is subject to a terminal disclaimer.

(21) Appl. No.: 15/298,155

(22) Filed: Oct. 19, 2016

(65) Prior Publication Data

US 2017/0137497 A1 May 18, 2017

Related U.S. Application Data (63) Continuation of application No. 12/599,703, filed as application No. PCT/EP2008/004231 on May 28, 2008, now Pat. No. 9,493,548.

(30) Foreign Application Priority Data

Jun. 1, 2007 (EP) .................................... 07010840

(51) Int. Cl.
*C07K 16/32* (2006.01)
*C07K 16/06* (2006.01)
*C07K 16/24* (2006.01)

(52) U.S. Cl.
CPC .......... *C07K 16/065* (2013.01); *C07K 16/244* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 4,889,632 A | 12/1989 | Svec et al. | |
| 4,895,806 A | 1/1990 | Le et al. | |
| 4,923,610 A | 5/1990 | Svec et al. | |
| 4,952,349 A | 8/1990 | Svec et al. | |
| 5,164,487 A | 9/1992 | Korthe et al. | |
| 5,610,285 A | 3/1997 | Lebing et al. | |
| 5,677,171 A | 10/1997 | Hudziak et al. | |
| 6,339,142 B1 | 1/2002 | Basey et al. | |
| 6,875,432 B2 | 4/2005 | Liu et al. | |
| 7,662,930 B2 | 2/2010 | Zhou | |
| 9,493,548 B2 * | 11/2016 | Falkenstein | C07K 16/065 |
| 2002/0064526 A1 | 5/2002 | Pollack | |
| 2005/0014245 A1 | 1/2005 | Hebel et al. | |
| 2006/0194953 A1 | 8/2006 | Bonnerjea et al. | |
| 2010/0069617 A1 | 3/2010 | Gagnon | |
| 2014/0142283 A1 | 5/2014 | Baehner et al. | |
| 2014/0243508 A1 | 8/2014 | Falkenstein et al. | |

FOREIGN PATENT DOCUMENTS

| | | |
|---|---|---|
| EP | 0447585 B2 | 5/2003 |
| EP | 07010840.2 | 12/2008 |
| JP | 7155194 | 6/1995 |
| WO | 2005/082926 A1 | 9/2005 |
| WO | 2006/024497 | 3/2006 |
| WO | 2006058623 A1 | 6/2006 |
| WO | 2006/096489 | 9/2006 |
| WO | 2008/145351 | 12/2008 |

OTHER PUBLICATIONS

Declaration of Dr. Meinhard Hasslacher dated Aug. 3, 2016, in the opposition to realted European Patent No. EP 2152745 (7 pages).
Declaration of Dr. Roberto Falkenstein dated Nov. 16, 2016, including Exhibits A and B, in the opposition to realted European Patent No. EP 2152745 (16 pages).
Second Declaration of Dr. Gregory S. Blank dated Nov. 25, 2015, in the opposition to realted European Patent No. EP 2152745 (1 page).
"A Guide to Conductivity and Dissolved Oxygen—the theory and practice of conductivity and dissolved oxygen measurement", Mettler Toledo.
"A Guide to Conductivity Measurement—Theory and Practice of Conductivity Applications", Mettler Toledo (2013).
Cutler (Ed.), "Protein Purification Protocols—Second Edition", Humana Press, pp. 6-7, 91-99, 125-131, 455-462, and 476-477 (2004).
Deutscher (Ed.), "Guide to Protein Purification, vol. 182, Methods in Enzymology", Academic Press, UBT017055773542.
Google cache for "A Guide to Conductivity and Dissolved Oxygen—the theory and practice of conductivity and dissolved oxygen measurement", Mettler Toledo, dated May 25, 1999.
Google search result for "guide to conductivity" dated May 25, 1999, printed Dec. 14, 2015.
Scopes, "Protein Purification: Principles and Practice—Third Edition", Springer-Verlag, pp. 135-136, 146-171, 185-186, and 324-335 (1982).
"Standard KCl solutions for calibrating conductivity cells—CRC Handbook of Chemistry and Physics" 93rd Edition (2002).
Abstract: Database WPI Week 199533, Thomson Scientific, London, 1995-250742; XP002283061, Purification of Proteins esp. monoclonal antibodies by using cation exchange resin, affinity chromatography, and anion exchange resin, with specific pH and concn. Of eluate.
Anonymous, "Protein Fractionation (Complexity Reduction) 2.2.2. 2. Mustang Ion Exchange Membrane", Pall Life Sciences, XP-002449753 (2005) (7 pages).

(Continued)

Primary Examiner — Yunsoo Kim (57) ABSTRACT

The current invention reports a method for purifying an immunoglobulin, wherein the method comprises applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material.

24 Claims, 5 Drawing Sheets

(56) References Cited

OTHER PUBLICATIONS

Avramescu et al., "Dynamic behavior of adsorber membranes for protein recovery", Biotechnol. Bioeng. 84(5): 564-572 (2003).
Conductance Data for Commonly Used Chemicals, Dec. 2010.
Conductivity ordering guide, Oct. 3, 1999.
CRC Handbook of Chemistry and Physics, 84th Edition, pp. 5-94 (2004).
Declaration of Dr. Gregory Blank, attached to the Reply of the patent proprietor to the notice(s) of opposition, dated May 22, 2015, in the opposition to realted European Patent No. EP 2152745 (34 pages).
Demmer et al., "Large-scale membrane adsorbers", J. Chromatogr. A, 852:73-81 (1999).
Document (D32) attached to the Reply of the patent proprietor to the notice(s) of opposition, dated May 22, 2015, in the opposition to related European Patent No. EP 2152745 (3 pages).
Document (D33) attached to the Reply of the patent proprietor to the notice(s) of opposition, dated May 22, 2015, in the opposition to related European Patent No. EP 2152745 (1 page).
Document (D35) attached to the Reply of the patent proprietor to the notice(s) of opposition, dated May 22, 2015, in the opposition to related European Patent No. EP 2152745 (1 page).
European Office Action in Corresponding Application 087588158.8—dated Jul. 22, 2011.
Fahrner et al., "Industrial purification of pharmaceutical antibodies: development, operation, and validation of chromatography processes", Biotechnol Genet Eng Rev., 18:301-327 (2001).
Fischer-Fruehholz et al., "Applications Sartobind Membrane Adsorbers", Internet Presentation (2007).
Fischer-Fruehholz et al., "Applications Sartobind Membrane Adsorbers", Internet Presentation (2006).
Fischer-Fruhholz et al., Internet Article: Applications Sartobind Membrane Adsorbers, XP002449752, p. 30 (2007).
Gagnon et al., "The practical task of monoclonal IgG purification with CHT ceramic hydroxyapatite", 11th Annual Waterside Conference (2006).
Ghosh, "Protein separation using membrane chromatography: opportunities and challenges", J. Chromatog. A, 952 (1-2):13-27 (2002).
Gottschalk et al., Bioprocess, 57-64 (2004).
Guidelines for Examination in the European Patent Office, Dec. 2007-Nov. 2014 (13 pages).
Hamilton, "The Human IgG Subclasses", Calbbiochem—Novabiochem Corporation (2001).
Himmelhoch, "Chromatography of proteins on ion-exchange adsorbents", Meth. Enzymol., 22:273-286 (1971).
HPLC of Biological Macromolecules, 2nd Edition, Eds K M Gooding & FE Regnier, Marcel Dekker, cover page and pp. 617-619 (2002).
Josic et al., Food Technol. Biotechnol 39:215-226 (2001).
Knudsen et al., "Membrane ion-exchange chromatography for process-scale antibody purification", J Chromatogr A., 907(1-2):145-154 (2001).
Luetkemeyer et al., "Membrane chromatography for rapid purification of recombinant antithrombin III and monoclonal antibodies from cell culture supernatant" J. Chromatogr, 639:57-66 (1993).
Marshak et al., "Strategies for protein purification and characterization—a laboratory cause manual" Cold Spring Harbor Laboratory Press, 54-58 (1996).
McPherson, Water/Engineering & Management, pp. 36, 37 and 44 (1997).
Nakamura et al., PREP 2007, including the brochure for the symposium at which the poster was presented (2007).
Opposition against EP 2152745 by Baxter on Oct. 16, 2014.
Opposition against EP 2152745 by onGregor Steglich, Oct. 8, 2014.
Opposition against EP 2152745 by Potter Clarkson on Oct. 16, 2014.
Petsch et al., "Membrane adsorbers for selective removal of bacterial endotoxin", J. Chromatogr. B 693:79-91 (1997).
Phillips et al., "Performance of a membrane adsorber for trace impurity removal in biotechnology manufacturing", J. Chromatogr. A, 1078:74-82 (2005).
Reif et al., "Characterization and application of strong ion-exchange membrane adsorbers as stationary phases in high-performance liquid chromatography of proteins", J. Chromatogr. A, 654:29-41 (1993).
Reis et al., "Membrane separations in biotechnology", Curr. Opinion Biotech., 12(2):208-211 (2001).
Roos, "Chapter 1: Ion Exchange Chromatography", In: J. Chromatogr. Lib., 61:3-88 (1999).
Roper et al., "Separation of biomolecules using adsorptive membranes", J. Chromatogr. A, 702:3-26 (1995).
Sarfert et al., "Mass transfer limitations in protein separations using ion-exchange membranes", J. Chromatogr. A, 764:3-20 (1997).
Suck et al., "Fast and efficient protein purification using membrane adsorber systems", J. Biotechnol., 121:361-367 (2006).
Takahashi et al., "Cationic charge-preferential IgG reabsorption in the renal proximal tubules", Kidney International, 66(4):1556-1560 (2004).
Thommes et al., "Membrane chromatography—an integrative concept in the downstream processing of proteins", Biotechnol. Prog. 11:357-367 (1995).
Tijssen, "Practice and theory of enzyme immunoassays", Elsevier, New York, 108-121 (1990).
Zapata, "Membrane chromatography for purification of human antibodies in commercial processes", presentation at IBC Antibody Meeting, Munich (2005).
Zeng et al., "Membrane chromatography: preparation and applications to protein separation", Biotechnol. Prog., 15:1003-1019 (1999).
Zhou et al., "New Q membrane scale-down model for process-scale antibody purification", J. Chromatogr. A, 1134:66-73 (2006).

* cited by examiner

IMMUNOGLOBULIN PURIFICATION

CROSS-REFERENCE TO RELATED APPLICATIONS

This application is a continuation of U.S. patent application Ser. No. 12/599,703, filed Nov. 11, 2009, which is U.S. National Stage Application under 35 U.S.C. § 371 of International Patent Application No. PCT/EP2008/004231, filed May 28, 2008, which claims the benefit of priority of European Patent Application No. EP07010840.2, filed Jun. 1, 2007, the content of each of which is incorporated by reference herein in its entirety.

The current invention is in the field of purification of polypeptides. It is reported a method for providing an immunoglobulin in monomeric form by separating the immunoglobulin in solution from impurities, especially from the immunoglobulin in aggregated form.

BACKGROUND OF THE INVENTION

Proteins and especially immunoglobulins play an important role in today's medical portfolio. For human application every therapeutic protein has to meet distinct criteria. To ensure the safety of biopharmaceutical agents to humans nucleic acids, viruses, and host cell proteins, which would cause severe harm, have to be removed especially. To meet these regulatory specifications one or more purification steps have to follow the manufacturing process. Among other things, purity, throughput, and yield play an important role in determining an appropriate purification process.

Different methods are well established and widespread used for protein purification, such as affinity chromatography with microbial proteins (e.g. protein A or protein G affinity chromatography), ion exchange chromatography (e.g. cation exchange (sulfopropyl or carboxymethyl resins), anion exchange (amino ethyl resins) and mixed-mode ion exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

Necina, R., et al. (Biotechnol. Bioeng. 60 (1998) 689-698) reported the capture of human monoclonal antibodies directly from cell culture supernatants by ion exchange media exhibiting high charge density. In WO 89/05157 a method is reported for the purification of product immunoglobulins by directly subjecting the cell culture medium to a cation exchange treatment. A one-step purification of monoclonal IgG antibodies from mouse ascites is described by Danielsson, A., et al., J. Immun. Meth. 115 (1988), 79-88.

Mhatre, R. et al. (J. Chrom. A 707 (1995) 225-231), explored the purification of antibody Fab fragments by cation exchange chromatography and pH gradient elution. WO 94/00561 reports human monoclonal anti-rhesus antibodies and cell lines producing the same. A method for purifying a polypeptide by ion exchange chromatography is reported in WO 2004/024866 in which a gradient wash is used to resolve a polypeptide of interest from one or more contaminants. Schwarz, A. et al. (Laborpraxis 21 (1997) 62-66) report the purification of monoclonal antibodies with a CM-HyperD-column.

WO 2004/076485 reports a process for antibody purification by protein A and ion exchange chromatography. In EP 0 530 447 a process for purifying IgG monoclonal antibodies by a combination of three chromatographic steps is reported. The removal of protein A from antibody preparations is reported in U.S. Pat. No. 4,983,722.

Recombinant monoclonal antibody processes often employ anion-exchange chromatography to bind trace levels of impurities and potential contaminants such as DNA, host cell protein, and virus, while allowing the antibody to flow through (Knudsen, H. L., et al., J. Chrom. A 907 (2001) 145-154).

WO 95/16037 reports the purification of anti-EGF-R/anti-CD3 bispecific monoclonal antibodies from hybrid hybridoma performed by protein A cation exchange chromatography. The separation of antibody monomers from its multimers by use of ion exchange chromatography is reported in EP 1 084 136. U.S. Pat. No. 5,429,746 relates to the application of hydrophobic interaction chromatography combination chromatography to the purification of antibody molecule proteins.

An anionic modified microporous membrane for use for the filtration of fluids, particular parenteral or biological liquids contaminated with charged particulates, is reported in U.S. Pat. No. 4,604,208. WO 03/040166 reports a membrane and a device designed for the removal of trace impurities in protein containing streams.

A method for recovering a polypeptide is reported in U.S. Pat. No. 6,716,598. In US 2006/0194953 is reported a method for selectively removing leaked protein A from antibody purified by means of protein A affinity chromatography.

SUMMARY OF THE INVENTION

The current invention comprises multiple aspects in the field of immunoglobulin purification. One aspect is a method for purifying an immunoglobulin comprising the step of applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material. In one embodiment said step is a chromatographic step operated in flow through mode.

In one embodiment comprises the method according to the invention a further step, either prior to or after the cation exchange step, of applying an aqueous, buffered solution comprising an immunoglobulin in monomeric form and/or in aggregated form to an anion exchange material under conditions whereby the immunoglobulin does not bind to the anion exchange material, and recovering the immunoglobulin from the flow-through of the anion exchange material. In one embodiment said step is a chromatographic step operated in flow-through mode.

In another embodiment comprises the method according to the invention either prior to the cation exchange step or prior to the anion exchange step the further step of applying an aqueous, buffered solution comprising the immunoglobulin in monomeric and in aggregated form to an affinity column under conditions whereby the immunoglobulin binds to the affinity column, and recovering the immunoglobulin in monomeric and in aggregated form from the affinity column. In one embodiment said step is a chromatographic step operated in bind-and-elute mode.

In a further embodiment of the method according to the current invention comprises the method as the cation exchange step the step of applying an aqueous, buffered solution comprising the immunoglobulin in monomeric and in aggregated form to a membrane cation exchange material under conditions whereby the immunoglobulin in monomeric form does not bind to the membrane cation exchange material, and recovering the immunoglobulin in monomeric form from the flow-through of the membrane cation exchange material. In one embodiment said cation exchange material is a membrane cation exchange material. In another embodiment the membrane cation exchange material is Mustang™ S, Mustang™ C, Sartobind™ S, or Sartobind™ C. In still another embodiment membrane cation exchange material is a polyethersulfone based membrane or a regenerated cellulose based membrane modified with sulfonic acid groups or carboxymethyl groups. In one embodiment the solution has a pH value of from pH 4 to pH 8, preferably of pH 5 to pH 8. In still another embodiment the solution has a conductivity of from 1 mS/cm to 15 mS/cm, preferably of from 4.0 mS/cm to 10.0 mS/cm.

Another embodiment comprises that recovering said immunoglobulin in monomeric form from the flow-through is by a method selected from precipitation, salting out, ultrafiltration, diafiltration, lyophilization, affinity chromatography, or solvent volume reduction to obtain a concentrated solution. Preferably said recovering is by ultrafiltration, lyophilization, or solvent volume reduction.

In another embodiment said immunoglobulin is obtained from the flow-through of the membrane cation exchange material and at least 95% of the immunoglobulin is in monomeric form. In still another embodiment at least 90% of the immunoglobulin in monomeric form does not bind to the cation exchange material. One embodiment is that the aqueous, buffered solution is a solution comprising phosphoric acid or salts thereof, citric acid or salts thereof, or histidine or salts thereof. In another embodiment the aqueous, buffered solution comprises sodium chloride or potassium chloride. And in still another embodiment the chromatographic step is a column chromatography or a cassette chromatography.

DETAILED DESCRIPTION OF THE INVENTION

The current invention comprises a method for purifying an immunoglobulin comprising the step of applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution or supernatant after the contact with, i.e. after the removal of, the cation exchange material.

The term "ion exchange material" or grammatical equivalents thereof as used within this application denotes an immobile high molecular weight matrix that carries covalently bound charged substituents. For overall charge neutrality not covalently bound counter ions are bound to the charged substituents by ionic interaction. The "ion exchange material" has the ability to exchange its not covalently bound counter ions for similarly charged binding partners or ions of the surrounding solution. Depending on the charge of its exchangeable counter ions the "ion exchange material" is referred to as "cation exchange material" or as "anion exchange material". Depending on the nature of the charged group (substituent) the "ion exchange material" is referred to as, e.g. in the case of cation exchange materials, sulfonic acid or sulfopropyl resin (S), or carboxymethyl resin (CM). Depending on the chemical nature of the charged group/substituent the "ion exchange material" can additionally be classified as strong or weak ion exchange material, depending on the strength of the covalently bound charged substituent. For example, strong cation exchange materials have a sulfonic acid group, preferably a sulfopropyl group, as charged substituent, weak cation exchange materials have a carboxylic acid group, preferably a carboxymethyl group, as charged substituent. Strong anion exchange materials have a quarternary ammonium group, and weak anion exchange materials have a diethylaminoethyl group as charged substituent.

The term "membrane" as used within this application denotes both a microporous or macroporous membrane. The membrane itself is composed of a polymeric material such as, e.g. polyethylene, polypropylene, ethylene vinyl acetate copolymers, polytetrafluoroethylene, polycarbonate, poly vinyl chloride, polyamides (nylon, e.g. Zetapore™, $N_{66}$ Posidyne™), polyesters, cellulose acetate, regenerated cellulose, cellulose composites, polysulphones, polyethersulfones, polyarylsulphones, polyphenylsulphones, polyacrylonitrile, polyvinylidene fluoride, non-woven and woven fabrics (e.g. Tyvek®), fibrous material, or of an inorganic material such as zeolithe, $SiO_2$, $Al_2O_3$, $TiO_2$, or hydroxyapatite. In one embodiment is the membrane a polyethersulfone membrane or a regenerated cellulose membrane.

Ion exchange resins are available under different names and from a multitude of companies such as e.g. cation exchange resins Bio-Rex® (e.g. type 70), Chelex® (e.g. type 100), Macro-Prep® (e.g. type CM, High S, 25 S), AG® (e.g. type 50 W, MP) all available from BioRad Laboratories, WCX 2 available from Ciphergen, Dowex® MAC-3 available from Dow chemical company, Mustang C and Mustang S available from Pall Corporation, Cellulose CM (e.g. type 23, 52), hyper-D, partisphere available from Whatman plc., Amberlite® IRC (e.g. type 76, 747, 748), Amberlite® GT 73, Toyopearl® (e.g. type SP, CM, 650M) all available from Tosoh Bioscience GmbH, CM 1500 and CM 3000 available from BioChrom Labs, SP-Sepharose™, CM-Sepharose™ available from GE Healthcare, Poros resins available from PerSeptive Biosystems, Asahipak ES (e.g. type 502C), CXpak P, IEC CM (e.g. type 825, 2825, 5025, LG), IEC SP (e.g. type 420N, 825), IEC QA (e.g. type LG, 825) available from Shoko America Inc., 50 W cation exchange resin available from Eichrom Technologies Inc., and such as e.g. anion exchange resins like Dowex® 1 available from Dow chemical company, AG® (e.g. type 1, 2, 4), Bio-Rex® 5, DEAE Bio-Gel 1, Macro-Prep® DEAE all available from BioRad Laboratories, anion exchange resin type 1 available from Eichrom Technologies Inc., Source Q, ANX Sepharose 4, DEAE Sepharose (e.g. type CL-6B, FF), Q Sepharose, Capto Q, Capto S all available from GE Healthcare, AX-300 available from PerkinElmer, Asahipak ES-502C, AXpak WA (e.g. type 624, G), IEC DEAE all available from Shoko America Inc., Amberlite® IRA-96, Toyopearl® DEAE, TSKgel DEAE all available from Tosoh Bioscience GmbH, Mustang Q available from Pall Corporation. In a membrane ion exchange material the binding sites can be found at the flow-through pore walls and not hidden within diffusion pores allowing the mass transfer via convection than diffusion. Membrane ion exchange materials are available under different names from some companies such as e.g. Sartorius (membrane cation exchange material: Sartobind™ CM, Sartobind™ S, membrane anion exchange material: Sartobind™ Q), or Pall Corporation (membrane cation exchange material: Mustang™ S, Mustang™ C, membrane anion exchange material: Mustang™ Q), or Pall BioPharmaceuticals. In one embodiment the membrane cation exchange material is Sartobind™ CM, or Sartobind™ S, or Mustang™ S, or Mustang™ C. In another embodiment the membrane cation exchange material is a polyethersulfone based membrane or a regenerated cellulose based membrane modified with sulfonic acid groups or carboxymethyl groups. In still another embodiment the anion exchange material is a Q-type (quarterny ammonium group-type) membrane anion exchange material or Q-anion exchange column.

A "polypeptide" is a polymer of amino acid residues joined by peptide bonds, whether produced naturally or synthetically. Polypeptides of less than about 20 amino acid residues are referred tom, as "peptides."

A "protein" is a macromolecule comprising one or more polypeptide chains or a polypeptide chain of more than 100 amino acid residues. A protein may also comprise non-peptidic components, such as carbohydrate groups. Carbohydrate groups and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "immunoglobulin" and grammatical equivalents thereof which can be used interchangeably within this application comprise at least two light polypeptide chains and two heavy polypeptide chains. Each of the heavy and light polypeptide chains contains a variable region (generally the amino terminal portion of the polypeptide chains) which contains a binding domain for interaction with an antigen. Each of the heavy and light polypeptide chains also comprises a constant region (generally the carboxyl terminal portion of the polypeptide chains) which may mediate the binding of the antibody to host tissue or factors including various cells of the immune system, some phagocytic cells and a first component (C1q) of the classical complement system. Typically, the light and heavy polypeptide chains are chains each consisting essentially of a variable region, i.e. $V_L$ or $V_H$, and a constant region, i.e. of $C_L$ in case of a light polypeptide chain, or of $C_H1$, hinge, $C_H2$, $C_H3$, and optionally $C_H4$ in case of a heavy polypeptide chain.

As used herein, the term "immunoglobulin" refers to a protein consisting of one or more polypeptides substantially encoded by immunoglobulin genes. The recognized immunoglobulin genes include the different constant region genes as well as the myriad immunoglobulin variable region genes. Immunoglobulins may exist in a variety of forms, including, for example, Fv, Fab, and F(ab)$_2$ as well as single chains (e.g. Huston, J. S., et al., Proc. Natl. Acad. Sci. USA 85 (1988) 5879-5883; Bird, R. E., et al., Science 242 (1988) 423-426; and, in general, Hood et al., Immunology, Benjamin N.Y., 2nd edition (1984); and Hunkapiller, T., and Hood, L., Nature 323 (1986) 15-16). In one embodiment immunoglobulins according to the invention comprise monoclonal antibodies and fragments thereof, for example isolated heavy or light chains, or heavy or light chains fused to a further peptide or polypeptide, and as well fragments thereof.

The term "immunoglobulin in monomeric form" and grammatical equivalents thereof denotes an immunoglobulin molecule which is not associated with a second immunoglobulin molecule, i.e. the immunoglobulin molecule is neither covalently nor non-covalently bound to a second immunoglobulin molecule. The term "immunoglobulin in aggregated form" and grammatical equivalents thereof denotes an immunoglobulin molecule which is associated, either covalently or non-covalently, with at least one additional immunoglobulin molecule. An immunoglobulin in aggregated form is eluted as a single peak from a size exclusion chromatography column. The term "in monomeric form" and grammatical equivalents thereof as used within this application not necessarily denotes that 100% of an immunoglobulin molecule are present in monomeric form. It furthermore denotes that of an immunoglobulin at least 90% of the immunoglobulin is in monomeric form, at least 95% of the immunoglobulin is in monomeric form, at least 98% of the immunoglobulin is in monomeric form, at least 99% of the immunoglobulin is in monomeric form, or more than 99% of the immunoglobulin is in monomeric form. The term "in monomeric and in aggregated form" denotes a mixture of immunoglobulin molecules not associated with other immunoglobulin molecules and of immunoglobulin molecules associated with other immunoglobulin molecules. In this mixture neither of the monomeric form nor the aggregated form is present exclusively.

The term "100%" as used within this application denotes that the amount of components other than a specified component are below the detection limit of the referred to analytical method under the specified conditions.

The terms "90%", "95%", "98%", "99%" as used within this application denote no exact values but values within the accuracy of the referred to analytical method under the specified conditions.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

For the purification of recombinantly produced immunoglobulins often a combination of different column chromatographical steps is employed. Generally a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step often an anion exchange material in a flow-through mode is used.

The term "flow-through mode" and grammatical equivalents thereof as used within the current invention denotes an operation mode of a purification method, e.g. a chromatographic method, in which a solution containing a substance of interest, e.g. an immunoglobulin in monomeric form, to be purified is brought in contact with a stationary, preferably solid, phase whereby the substance of interest does not bind to that stationary phase. As a result the substance of interest is obtained either in the flow-through (if the purification method is a chromatographical method) or the supernatant (if the purification method is a batch method). Substances not of interest, e.g. an immunoglobulin in aggregated form, which were also present in the solution, bind to the stationary phase and are in that way removed from the solution. This does not necessarily denote that 100% of the substances not of interest are removed from the solution but essentially 100% of the substances not of interest are removed, i.e. at least 50% of the substances not of interest are removed from the solution, at least 75% of the substances not of interest are removed the from solution, at least 90% of the substances not of interest are removed from the solution, or more than 95% of the substances not of interest are removed from the solution.

The term "applying to" and grammatical equivalents thereof as used within this application denotes a partial sip of a purification method, in which, a solution containing a substance of interest to be purified is brought in contact with a stationary phase. This denotes that a) the solution is added to a chromatographic device in which the stationary phase is located, or b) that a stationary phase is added to the solution. In case a) the solution containing the substance of interest to be purified passes through the stationary phase allowing for an interaction between the stationary phase and the substances in solution. Depending on the conditions, such as e.g. pH, conductivity, salt concentration, temperature, and/or flow rate, some substances of the solution are bound to the stationary phase and thus are removed from the solution. Other substances remain in solution. The substances remaining in solution can be found in the flow-through. The "flow-through" denotes the solution obtained after the passage of the chromatographic device. Preferably the chromatographic device is a column, or a cassette. In one embodiment the chromatographic step is a column chromatography, i.e. a chromatographic step using a solid phase in a column, or a cassette chromatography, i.e. a chromatographic step using a solid phase in a cassette. In preferred embodiment the cassette chromatography employs a membrane in a cassette. The substance of interest not bound to the stationary phase can be recovered in one embodiment from the flow-though by methods familiar to a person of skill in the art, such as e.g. precipitation, salting out, ultrafiltration, diafiltration, lyophilization, affinity chromatography, or solvent volume reduction to obtain a concentrated solution. In a preferred embodiment is the immunoglobulin in monomeric form recovered from the flow-through by lyophilization, ultrafiltration, or solvent volume reduction. In case b) the stationary phase is added, e.g. as a powder, to the solution containing the substance of interest to be purified allowing for an interaction between the stationary phase and the substances in solution. After the interaction the stationary phase in removed, e.g. by filtration, and the substance of interest not bound to the stationary phase is obtained in the supernatant.

The term "does not bind to" and grammatical equivalents thereof as used within this application denotes that a substance of interest, e.g. an immunoglobulin, remains in solution when brought in contact with a stationary phase, e.g. an ion exchange material. This does not necessarily denote that 100% of the substance of interest remains in solution but essentially 100% of the substance of interest remains in solution, i.e. at least 50% of the substance of interest remains in solution and does not bind to the stationary phase, at least 65% of the substance of interest remains in solution and does not bind to the stationary phase, at least 80% of the substance of interest remains in solution and does not bind to the stationary phase, at least 90% of the substance of interest remains in solution and does not bind to the stationary phase, or more than 95% of the substance of interest remains in solution and does not bind to the stationary phase.

The term "buffered" as used within this application denotes a solution in which changes of pH due to the addition or release of acidic or basic substances is leveled by a buffer substance. A solution comprising a buffer substance is a "buffered solution". Any buffer substance resulting in such an effect can be used. In one embodiment pharmaceutically acceptable buffer substances are used, such as e.g. phosphoric acid and salts thereof, citric acid and salts thereof, morpholine, 2-(N-morpholino) ethanesulfonic acid and salts thereof, Histidine and salts thereof, Glycine and salts thereof, or tris (hydroxymethyl) aminomethane (TRIS) and salts thereof. In a preferred embodiment is the buffer substance phosphoric acid and/or salts thereof, citric acid and/or salts thereof, or histidine and/or salts thereof. Optionally the buffered solution may comprise an additional salt, such as e.g. sodium chloride, sodium sulphate, potassium chloride, potassium sulfate, sodium citrate, or potassium citrate. In one embodiment comprises the buffered solution sodium chloride or potassium chloride.

The term "bind-and-elute mode" as used in the current invention denotes an operation mode of a purification method, in which a solution containing a substance of interest to be purified is brought in contact with a stationary phase, preferably a solid phase, whereby the substance of interest binds to the stationary phase. As a result the substance of interest is retained on the stationary phase whereas substances not of interest are removed with the flow-through or the supernatant. The substance of interest is afterwards optionally after a washing step eluted from the stationary phase in a second step and thereby recovered from the stationary phase with an elution solution.

For the separation of immunoglobulins in monomeric form from immunoglobulins in aggregated form generally chromatographic methods employing cation exchange materials operated in a bind-and-elute mode are used, see e.g. WO 2006/125599. It has now surprisingly been found that cation exchange materials operated in a flow-through mode can be used for the removal of immunoglobulins in aggregated form from solutions containing immunoglobulins in monomeric and aggregated form. With this method for purifying an immunoglobulin it is possible to remove immunoglobulins in aggregated form in a fast and easy way from solutions containing a mixture of immunoglobulins both in monomeric form and in aggregated form.

Thus, the current invention reports a method for purifying an immunoglobulin, wherein the method comprises the following step:

a) applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material.

In more detail, the current invention comprises a method for obtaining an immunoglobulin in monomeric form from a solution comprising the immunoglobulin in monomeric and in aggregated form, whereby the method comprises the step of applying an aqueous, buffered solution comprising the immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material. In one embodiment said step is a chromatographic step operated in flow-through mode. In another embodiment is said cation exchange material a membrane cation exchange material.

The term "conditions under which the immunoglobulin in monomeric form does not bind to the cation exchange material" and grammatical equivalents thereof as used within this application denotes that an immunoglobulin in monomeric form remains in solution when brought in contact with the cation exchange material. This does not necessarily denote that 100% of the immunoglobulin in monomeric form remains in solution but essentially 100% of the immunoglobulin in monomeric form remains in solution and does not bind to the cation exchange material, i.e. at least 50% of the immunoglobulin in monomeric form remains in solution and does not bind to the cation exchange material, at least 65% of the immunoglobulin in monomeric form remains in solution and does not bind to the cation exchange material, at least 80% of the immunoglobulin in monomeric form remains in solution and does not bind to the cation exchange material, at least 90% of the immunoglobulin in monomeric form remains in solution and does not bind to the cation exchange material, or more than 95% of the immunoglobulin in monomeric form remains in solution and does not bind to the cation exchange material. Such conditions are e.g. in one embodiment a pH value of the aqueous, buffered solution of from pH 5 to pH 8 and/or in another embodiment a conductivity of the aqueous, buffered solution of from 1.0 mS/cm to 15 mS/cm, preferably of from 4.0 mS/cm to 10.0 mS/cm.

In one embodiment of the current invention comprises the method for purifying an immunoglobulin the step of applying an aqueous, buffered solution comprising the immunoglobulin in monomeric and in aggregated form to a membrane cation exchange material under conditions whereby the immunoglobulin in monomeric form does not bind to the membrane cation exchange material, and recovering the immunoglobulin in monomeric form from the flow-through of the membrane cation exchange material.

In this embodiment the purification method is a chromatographic method operated in flow-through mode, which allows for a rapid purification of the immunoglobulin, because the desired immunoglobulin in monomeric form can easily be obtained from the flow-through of the column, making further steps, such as washing of the column, elution of the bound substance, or desalting of the eluted immunoglobulin solution, unnecessary.

The method according to the invention can be employed as a single step method or combined with other steps, such as, e.g., in one embodiment with an anion exchange chromatography step, or with an affinity chromatography step in another embodiment.

Thus, one embodiment of the current invention is a method for purifying an immunoglobulin, wherein the method comprises the following sequential steps:

b) applying an aqueous, buffered solution comprising the immunoglobulin in monomeric and in aggregated form to an anion exchange chromatography column under conditions whereby the immunoglobulin does not bind to the anion exchange material, and recovering the immunoglobulin in monomeric and in aggregated form from the flow-through of the anion exchange column as an aqueous, buffered solution, and a) applying the aqueous, buffered solution obtained in step b) comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material.

In one embodiment step b) is a chromatographic method operated in flow-through mode. In another embodiment step a) is a chromatographic method operated in flow-through mode. In another embodiment is said cation exchange material in step a) a membrane cation exchange material. The conditions for step b) are known to a person of skill in the art. With step b) it is possible to reduce the amount of host cell protein (HCP), protein A, endotoxins, and/or viruses in the solution containing the immunoglobulin. It is also possible to reverse the order of the two ion exchange steps. Prior to the application of a solution to one step (or to a subsequent step) of a purification method parameters, such as e. g. the pH value or the conductivity of the solution, have to be adjusted. In one embodiment the pH value of the aqueous solution applied in step a) is of from pH 4 to pH 8, preferably of from pH 5 to pH 8. In an other embodiment the conductivity of the aqueous solution is of from 4.0 mS/cm to 10.0 mS/cm.

Additionally, the current invention comprises in one embodiment a method for purifying an immunoglobulin, wherein the method comprises the following sequential steps:

a) applying an aqueous, buffered solution comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material, and c) applying the aqueous, buffered solution of step a) comprising the immunoglobulin in monomeric form to an anion exchange chromatography column under conditions whereby the immunoglobulin does not bind to the anion exchange material, and recovering the immunoglobulin in monomeric form from the flow-through of the anion exchange chromatography column.

In one embodiment step c) is a chromatographic method operated in flow-through mode. In another embodiment step a) is a chromatographic method operated in flow-through mode. In another embodiment is said cation exchange material in step a) a membrane cation exchange material. It might be helpful e.g. to remove the bulk of the host cell proteins and culture by-products in a foremost purification step employing an affinity chromatography.

One embodiment of the current invention is a method comprising the following steps in this order:

d) applying an aqueous, buffered solution comprising the immunoglobulin in monomeric and in aggregated form to an affinity column under conditions whereby the immunoglobulin binds to the affinity column, and recovering the immunoglobulin in monomeric and in aggregated form from the affinity column as a aqueous, buffered solution, and b) optionally applying the aqueous, buffered solution obtained in step d) comprising the immunoglobulin in monomeric and in aggregated form to an anion exchange chromatography column under conditions whereby the immunoglobulin does not bind to the anion exchange material, and recovering the immunoglobulin in monomeric and in aggregated form from the flow-through of the anion exchange column as an aqueous, buffered solution, and a) applying the aqueous, buffered solution either obtained in step d) or obtained in step b) comprising an immunoglobulin in monomeric and in aggregated form to a cation exchange material under conditions whereby the immunoglobulin in monomeric form does not bind to the cation exchange material, and recovering the immunoglobulin in monomeric form from the solution after the contact with the cation exchange material.

In one embodiment step b) is a chromatographic method operated in flow-through mode. In another embodiment step a) is a chromatographic method operated in flow-through mode. In another embodiment step d) is operated in bind-and-elute mode. In another embodiment is said cation exchange material a membrane cation exchange material. The affinity column may e.g. be a protein A affinity column, a protein G affinity column, a hydrophobic charge induction chromatography column (HCIC), or a hydrophobic interaction chromatography column (HIC, e.g. with phenyl-sepharose, aza-arenophilic resins, or m-aminophenylboronic acid). Preferably the affinity column is a protein A column or a HCIC column.

In a further embodiment the aqueous buffered solution comprising the immunoglobulin in monomeric form and in aggregated form in step b) and/or the aqueous buffered solution comprising the immunoglobulin in monomeric form in step c) is applied to an anion exchange chromatography column under conditions whereby the immunoglobulin does bind to the anion exchange material, and is recovered from the anion exchange material as a aqueous, buffered solution.

One aspect of the invention is a method for obtaining an immunoglobulin in monomeric form from a solution comprising the immunoglobulin in monomeric and in aggregated form, whereby this method comprises the following step:

a) a chromatographic step operated in flow-through mode comprising applying an aqueous, buffered solution comprising the immunoglobulin in monomeric form and in aggregated form to a membrane cation exchange material under conditions whereby the immunoglobulin in monomeric form does not bind to the cation exchange material, the immunoglobulin in monomeric form is recovered from the flow-through of the membrane cation exchange material.

In one embodiment the method according to the invention comprises prior to step a) the following step:

b) a chromatographic step operated in flow-through mode comprising applying an aqueous, buffered solution comprising the immunoglobulin in monomeric form and in aggregated form to an anion exchange chromatography column under conditions whereby the immunoglobulin does not bind to the anion exchange material, and recovering the immunoglobulin in monomeric and in aggregated form from the flow-through of the anion exchange column as an aqueous, buffered solution.

In one embodiment the method according to the invention comprises after step a) the following step:

c) a chromatographic step operated in flow-through mode comprising applying the aqueous, buffered solution obtained in step a) comprising the immunoglobulin in monomeric form to an anion exchange chromatography column under conditions whereby the immunoglobulin does not bind to the anion exchange material, and recovering the immunoglobulin in monomeric form from the flow-through of the anion exchange chromatography column.

In another embodiment the method according to the invention comprises prior to step a) or step b) the following step:

d) a chromatographic step operated in bind-end-elute mode comprising applying an aqueous, buffered solution comprising the immunoglobulin in monomeric and in aggregated form to an affinity column under conditions whereby the immunoglobulin binds to the affinity column, and recovering the immunoglobulin in monomeric and in aggregated form from the affinity column as a aqueous, buffered solution.

In another embodiment the recovering said immunoglobulin in monomeric form from the flow-through is by a method selected from precipitation, salting out, ultrafiltration, diafiltration, lyophilization, affinity chromatography, or solvent volume reduction to obtain a concentrated solution. Preferably said recovering is by ultrafiltration, lyophilization, or solvent volume reduction.

In one embodiment the immunoglobulin is obtained from the flow-through of the membrane cation exchange material at least 95% of the immunoglobulin is in monomeric form. In another embodiment at least 90% of the immunoglobulin in monomeric form does not bind to the cation exchange material.

In still another embodiment the pH value of the aqueous, buffered solution is of from pH 5 to pH 8. In a further embodiment the conductivity of the aqueous, buffered solution of from 4.0 mS/cm to 10.0 mS/cm. In one embodiment the buffered solution is a solution comprising phosphoric acid or salts thereof, citric acid or salts thereof, or histidine or salts thereof. In still another embodiment the aqueous solution comprises sodium chloride or potassium chloride.

In one embodiment the membrane cation exchange material is a polyethersulfone based membrane or a regenerated cellulose based membrane modified with sulfonic acid groups or carboxymethyl groups. In a further embodiment the chromatographic step is a column chromatography or a cassette chromatography.

The following examples and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 2B: SEC analysis of fraction 2 of the flow-through.

EXAMPLES

Materials and Methods:
Conditioned Protein a Eluate:

An anti-(IL-13Rα1) antibody (hereinafter referred to as mAb IL13, see e.g. WO 2006/072564) and an anti-Her2 antibody (hereinafter referred to as mAb Her2, see e.g. U.S. Pat. No. 5,677,171) were purified in a first step with a protein A affinity chromatography.

The mAb IL13 was eluted from the protein A column under acidic conditions (3.5 mM hydrochloric acid, pH value 2.7±0.2). Before the filtration step the pH value of the fraction containing the immunoglobulin was adjusted with a concentrated, e.g. 1 M, buffer solution of pH 9.0 (e.g. tris (hydroxymethyl) amino-methane (TRIS) or phosphate buffer) to pH 5.0. This material is referred to in the following as conditioned protein A eluate of mAb IL13.

The mAb Her2 was purified in a first step with a protein A affinity chromatography. Elution from the protein A column is carried out under acidic conditions (10 mM sodium citrate buffer, pH value of 3.0±0.5). Before the filtration step the pH value of the fraction containing the immunoglobulin is adjusted with a concentrated tris (hydroxymethyl) aminomethane (TRIS) buffer to pH 5.6. This material is referred to in the following as conditioned protein A eluate of mAb Her2.

Analytical Methods:
Size Exclusion Chromatography:
resin: TSK 3000 (Tosohaas)
column: 300×7.8 mm
flow rate: 0.5 ml/min
buffer: 200 mM potassium phosphate containing 250 mM potassium chloride, adjusted to pH 7.0
wavelength: 280 nm
DNA-threshold-system: see e.g. Merrick, H., and Hawlitschek, G., Biotech Forum Europe 9 (1992) 398-403
Protein A ELISA: The wells of a micro titer plate are coated with a polyclonal anti-protein A-IgG derived from chicken. After binding non-reacted antibody is removed by washing with sample buffer. For protein A binding a defined sample volume is added to the wells. The protein A present in the sample is bound by the chicken antibody and retained in the wells of the plate. After the incubation the sample solution is removed and the wells are washed. For detection are added subsequently a chicken derived polyclonal anti-protein A-IgG-biotin conjugate and a Streptavidin peroxidase conjugate. After a further washing step substrate solution is added resulting in the formation of a colored reaction product. The intensity of the color is proportional to the protein A content of the sample. After a defined time the reaction is stopped and the absorbance is measured.
Host cell protein (HCP) ELISA:
The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

Example 1

Purification of mAb IL13 to Monomeric Form—Comparison of Conditions

In the purification of mAb IL13 to monomeric form different conditions were evaluated.

The purification method was operated as a chromatographic purification method in flow-through mode. Different conditions for the flow-through purification of the mAb IL13 were evaluated. As membrane cation exchange material the Mustang™ S-Adsorber System (Mustang™ S Coin, 1.5 cm² membrane area, Pall Corporation, USA) has been used.

The conditioned protein A eluate had a mAb IL13 concentration of 7.1 g/l with 90.9% of the immunoglobulin in monomeric form and 9.1% of the immunoglobulin in aggregated form. The conditioned protein A eluate has been virus inactivated and filtered through a 0.2 µm pore filter prior to the experiments. After dilution with the corresponding buffer to a protein concentration of approx. 1 mg/ml (a ratio of approx. 1:7 (v/v)), pH and conductivity adjustment, the solutions were applied to the membrane cation exchange material. If necessary the adjustment of pH was performed with potassium hydrogen phosphate or potassium dihydrogenphosphate and conductivity adjustment was done by the addition of KCl or deionized water (with pH of approx. 5.5 and 7.5, respectively). Such a diluted, adjusted, and conditioned protein A eluate is referred to in the following as sample material.

Diversified parameters were conductivity and pH. Observed parameters were yield and purity of the flow-through immunoglobulin in monomeric form of the sample material. The diversified parameters of the sample material are summarized in Table 1.

TABLE 1

Sample material parameters

| Sample No. | pH Value | buffer | conductivity [mS/cm] |
|---|---|---|---|
| 1 | 5.5 | 40 mM potassium phosphate | 4.8 |
| 2 | 6.5 | 40 mM potassium phosphate | 4.8 |
| 3 | 7.5 | 40 mM potassium phosphate | 4.8 |
| 4 | 5.5 | 50 mM potassium phosphate | 5.8 |
| 5 | 6.5 | 50 mM potassium phosphate | 5.8 |
| 6 | 7.5 | 50 mM potassium phosphate | 5.8 |
| 7 | 5.5 | 60 mM potassium phosphate | 6.8 |
| 8 | 6.5 | 60 mM potassium phosphate | 6.8 |
| 9 | 7.5 | 60 mM potassium phosphate | 6.8 |

Figure 1:
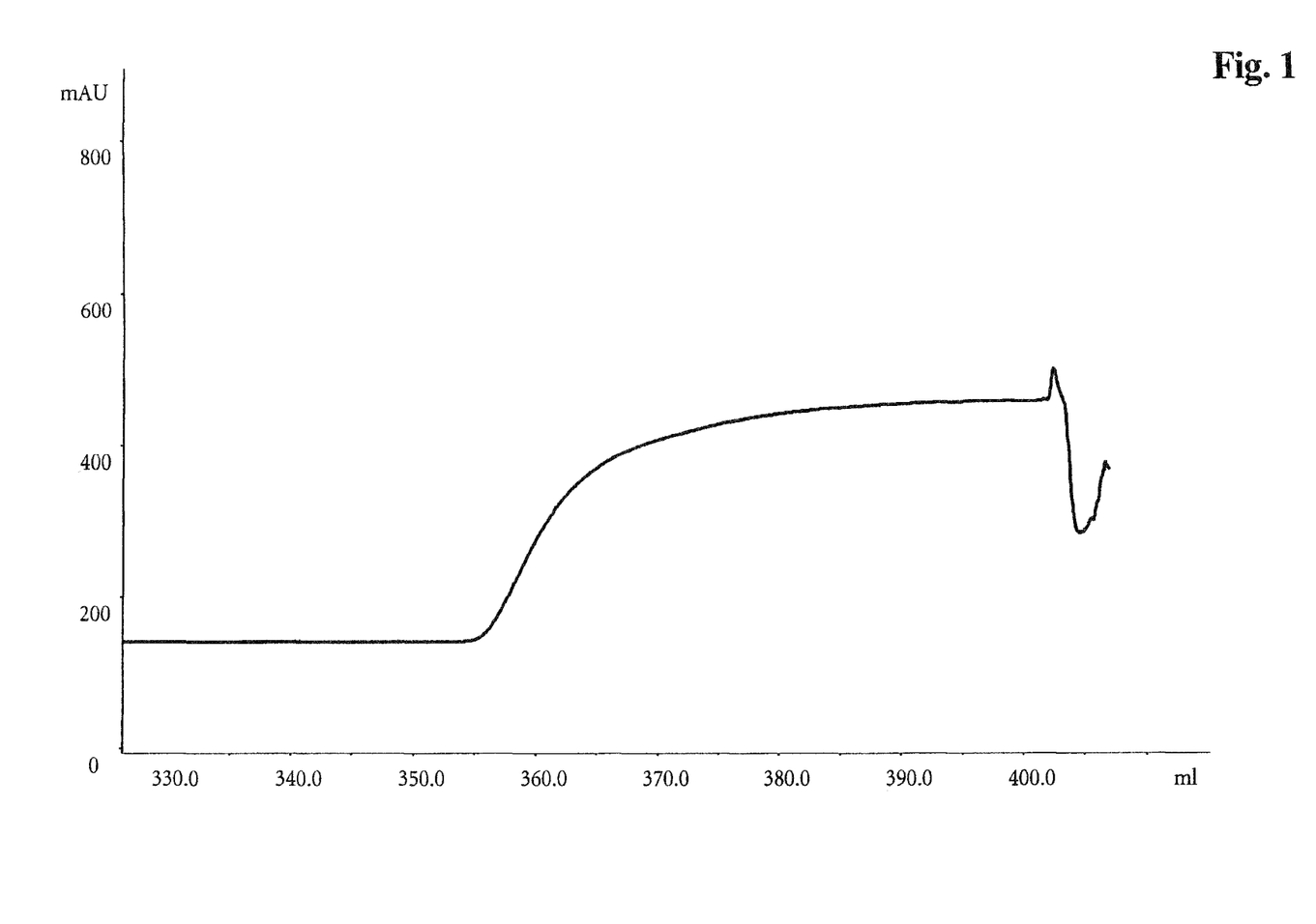
FIG. 1: Diagram of mAb IL13 flow-through mode purification with a Mustang™ S membrane.
Figure 2A:
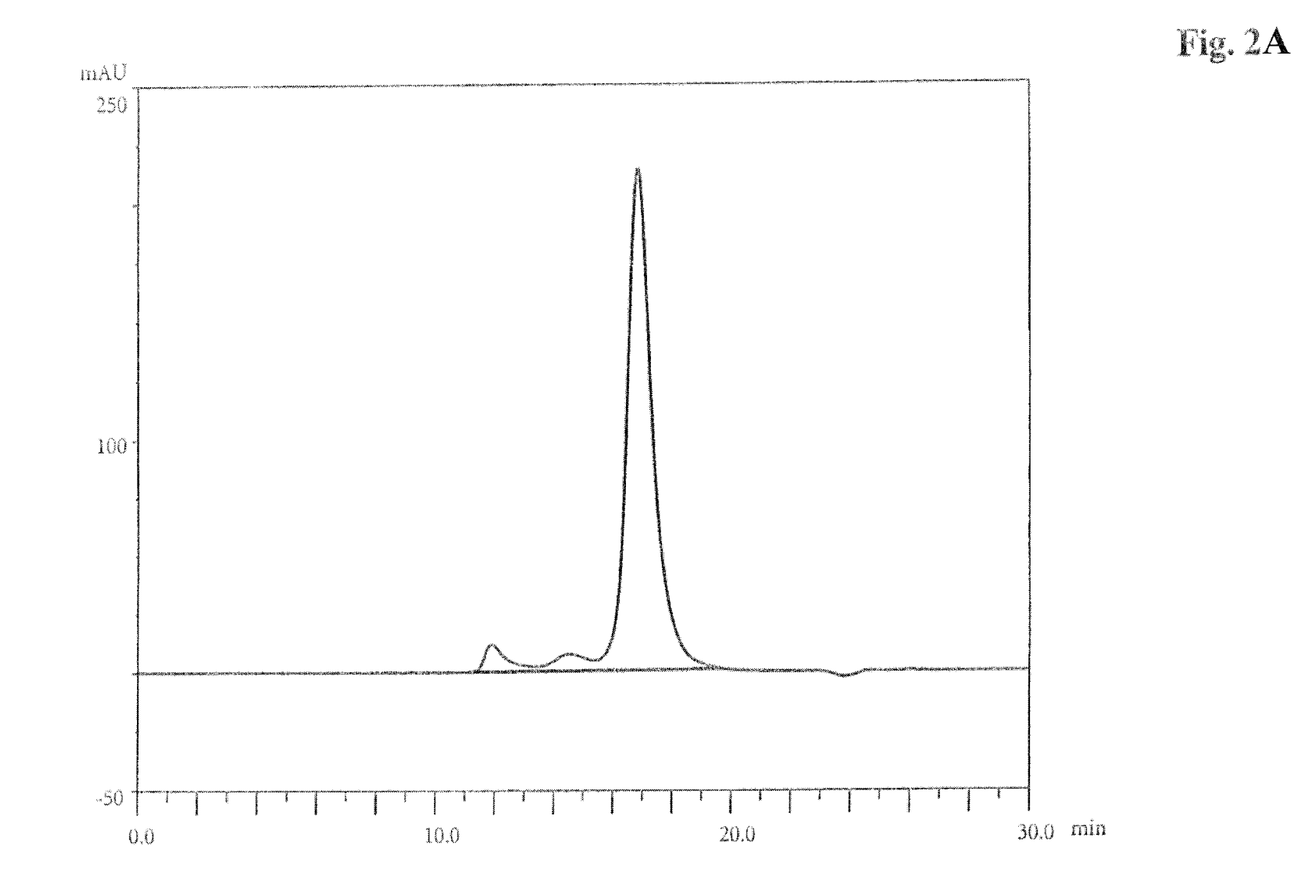
FIG. 2A: SEC (size exclusion chromatogram) analysis of the sample material mAb IL13.
Figure 2B:
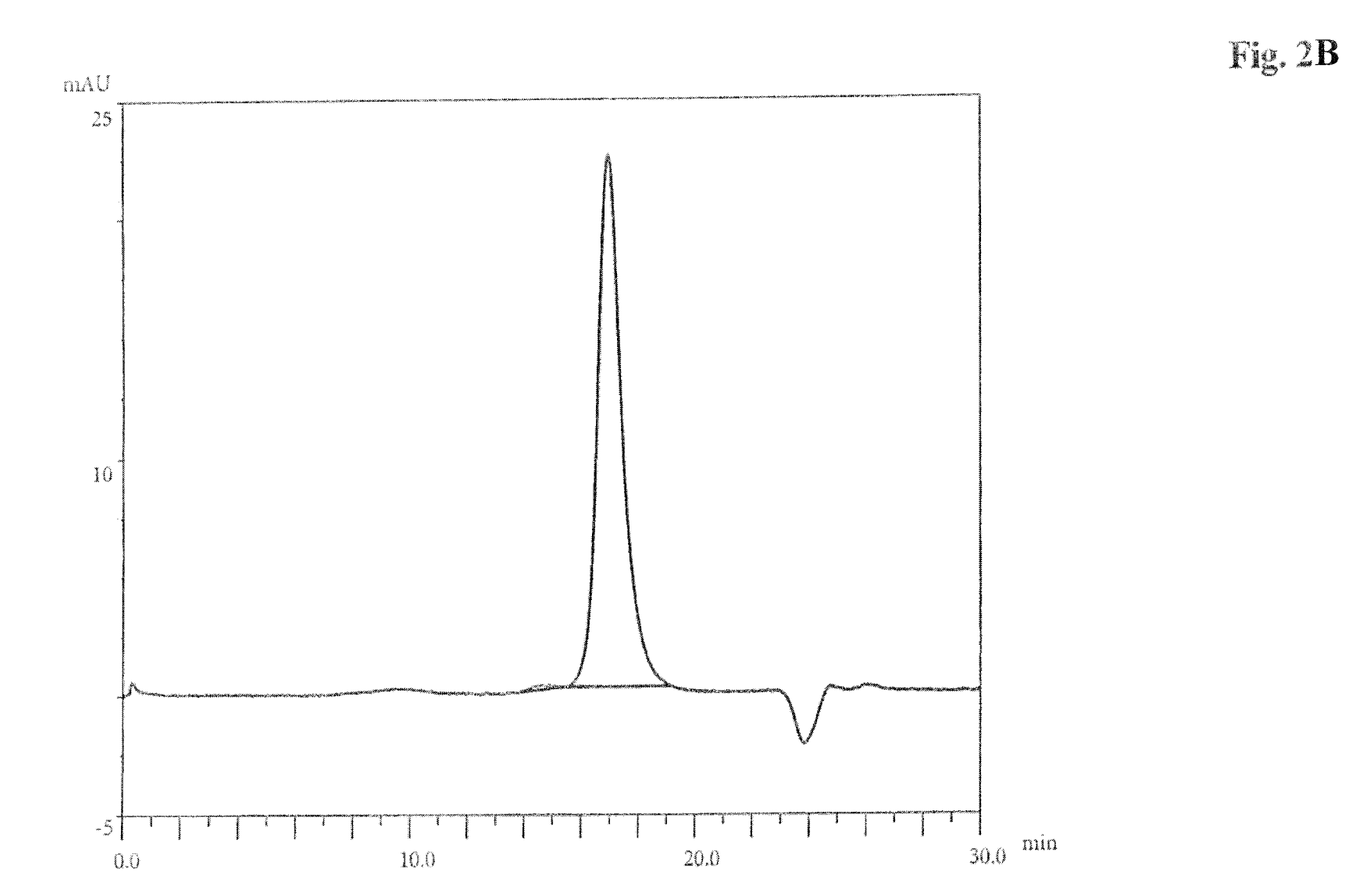

The flow-through has been analyzed by size exclusion chromatography in order to determine the amount of immunoglobulin in monomeric form and in aggregated form. The second fraction was chosen for analysis because in the beginning of the process (1$^{st}$ fraction) no stable purification process had established because due to the dead volume of the chromatographic system no steady flow exists and thus an unknown dilution of the 1$^{st}$ fraction occurs. An exemplary flow-through diagram is depicted in FIG. 1. The results are summarized in Table 2. The size exclusion chromatograms of the sample material and of fraction 2 (pH 6.5, 5.8 mS/cm) are shown in FIGS. 2A and 2B.

TABLE 2 mAb IL13 immunoglobulin in monomeric form (as area percentage of SEC chromatography) and yield with a Mustang ™ S membrane.

| | pH value | | | | | |
|---|---|---|---|---|---|---|
| | 5.5 | | 6.5 | | 7.5 | |
| conductivity [mS/cm] | mAb IL13 monomeric form | yield | mAb IL13 monomeric form | yield | mAb IL13 monomeric form | yield |
| 4.8 | 100% | 33.6% | 100% | 82.5% | 75% | 94.4% |
| 5.8 | 100% | 65.7% | 100% | 90.9% | 0% | 100% |
| 6.8 | 100% | 67.9% | 99% | 91.1% | 0% | — |

The data presented in Table 2 show that conditions suitable for the purification of mAb IL13, i.e. the separation of an immunoglobulin in monomeric form from the aggregated form, i.e. conditions under which the immunoglobulin in monomeric form does not bind to the membrane cation exchange material, with excellent yield can be adjusted, such as e.g. a conductivity of 5.8 mS/cm and a pH of 6.5.

Example 2

Purification of mAb IL13 to Monomeric Form—Comparison of Membranes

The results obtained in Example 1 are generally applicable and have been applied to the membrane cation exchange material Sartobind™ S (75 cm² membrane area, Sartorius AG, Göttingen, Germany). The preferred conditions for Mustang™ S, i.e. conductivity of 5.8 mS/cm at a pH of 6.5, were also applied to the Sartobind™ material. The sample material containing mAb IL13 had a protein concentration of 1.34 mg/ml with 94.8% of the immunoglobulin in monomeric form and 5.2% of the immunoglobulin in aggregated form. The sample material was applied to the membrane as reported in Example 1. The results of the purification process are summarized in Table 3.

TABLE 3 mAb IL13 immunoglobulin in monomeric and aggregated form (as area percentage of SEC chromatography) and yield with a Sartobind ™ S membrane.

| Sample No. | Sample amount of mAb IL13 | Sample volume | mAb IL13 in monomeric form in flow-through | | | | mAb IL13 in aggregated form in flow-through | |
|---|---|---|---|---|---|---|---|---|
| | | | total concentration | area percentage | amount | yield | area percentage | amount |
| 1 | 14.71 mg | 11 ml | 0.029 mg/ml | 100% | 1.02 mg | 6.9% | bdl | — |
| 2 | 14.71 mg | 11 ml | 0.51 mg/ml | 99% | 5.59 mg | 38.0% | 1.00% | 0.06 mg |
| 3 | 14.71 mg | 11 ml | 0.89 mg/ml | 97.6% | 9.54 mg | 64.9% | 2.45% | 0.24 mg |
| 4 | 14.71 mg | 11 ml | 0.94 mg/ml | 97.5% | 10.03 mg | 68.2% | 2.53% | 0.26 mg |
| 5 | 14.71 mg | 11 ml | 0.94 mg/ml | 97.8% | 10.11 mg | 68.7% | 2.17% | 0.22 mg |
| 6 | 14.71 mg | 11 ml | 0.94 mg/ml | 97.9% | 10.16 mg | 69.1% | 2.07% | 0.22 mg |
| 7 | 14.71 mg | 11 ml | 0.95 mg/ml | 97.5% | 10.14 mg | 68.9% | 2.54% | 0.26 mg |
| Average of samples 4 to 7 | 14.71 mg | 11 ml | 0.94 mg/ml | 97.7% | 10.11 mg | 68.7% | 2.33% | 0.24 mg | bdl = below detection limit

Figure 3:
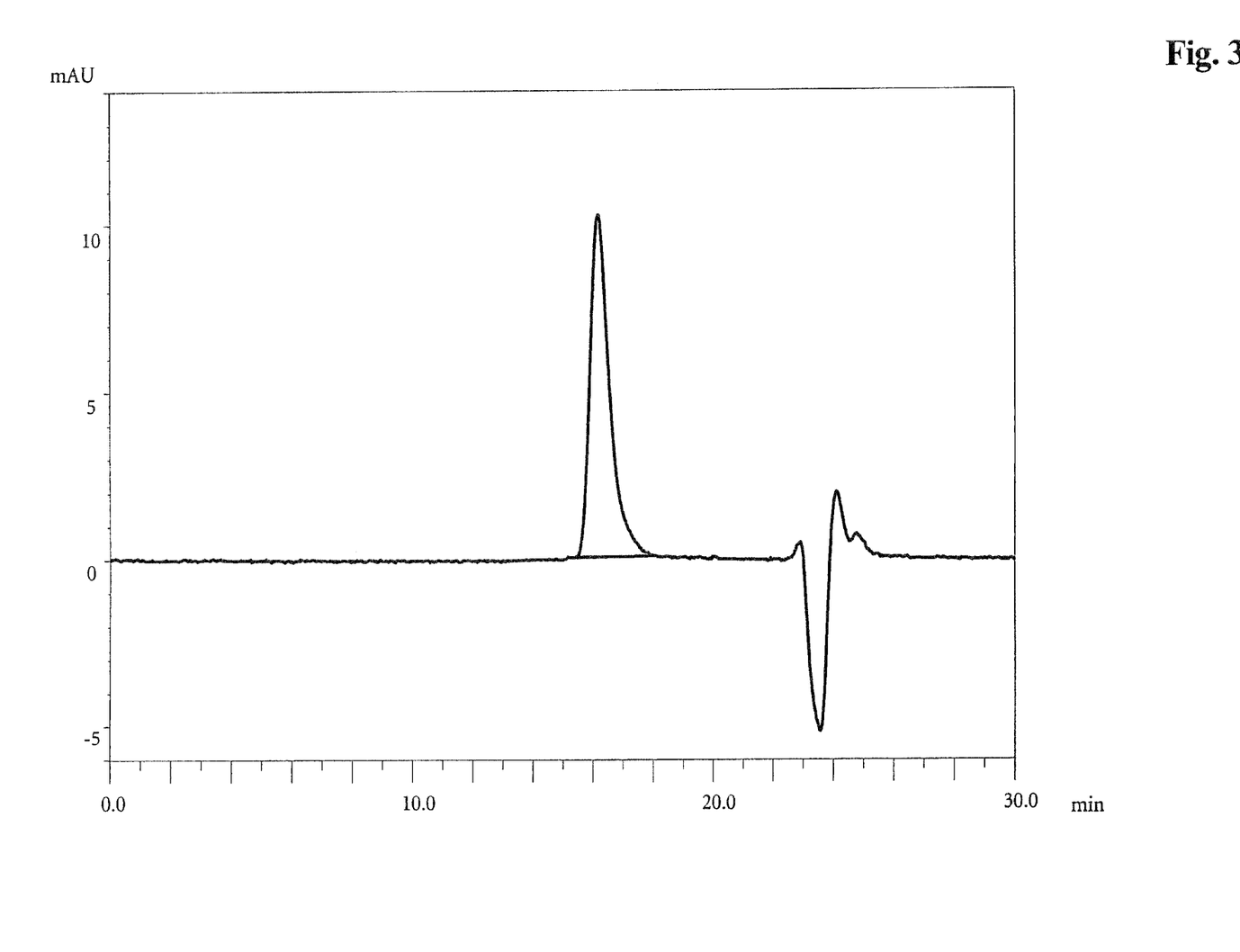
FIG. 3: SEC analysis of fraction 2 of the flow-through of a Sartobind™ C membrane process of sample material containing mAb IL13.

The same sample material was also applied to a Sartobind™ C membrane. The results are presented in Table 4 and an exemplary size exclusion chromatogram of the 3$^{rd}$ fraction is shown in FIG. 3.

TABLE 4 mAb IL13 immunoglobulin in monomeric and aggregated form (as area percentage of SEC chromatography) and yield with a Sartobind ™ C membrane.

| Sample No. | Sample amount of mAb IL13 | Sample volume | mAb IL13 in monomeric form in flow-through | | | | mAb IL13 in aggregated form in flow-through | |
|---|---|---|---|---|---|---|---|---|
| | | | total concentration | area percentage | amount | yield | area percentage | amount |
| 1 | 14.71 mg | 11 ml | 0 mg/ml | bdl | — | — | bdl | — |
| 2 | 14.71 mg | 11 ml | 0.033 mg/ml | 100% | 0.36 mg | 2.4% | bdl | — |
| 3 | 14.71 mg | 11 ml | 0.56 mg/ml | 100% | 6.15 mg | 41.8% | bdl | — |
| 4 | 14.71 mg | 11 ml | 0.87 mg/ml | 99.4% | 9.54 mg | 64.9% | 0.65% | 0.06 mg |
| 5 | 14.71 mg | 11 ml | 0.93 mg/ml | 99.3% | 10.20 mg | 69.3% | 0.66% | 0.07 mg |
| 6 | 14.71 mg | 11 ml | 0.96 mg/ml | 98.9% | 10.43 mg | 70.9% | 1.13% | 0.12 mg |
| 7 | 14.71 mg | 11 ml | 0.98 mg/ml | 98.9% | 10.66 mg | 72.5% | 1.08% | 0.12 mg |
| Average of samples 4 to 7 | 14.71 mg | 11 ml | 0.94 mg/ml | 99.1% | 10.21 mg | 69.4% | 0.88% | 0.09 mg | bdl = below detection limit
— = not determined

By using the purification conditions determined with one membrane material in all experiments, all cationic membrane adsorbers demonstrated will have the capability to remove aggregates and to obtain monomeric IgG in flow-through mode operation with the same conditions.

Example 3

Purification of mAb Her2 to Monomeric Form—Comparison of Membranes

The conditioned protein A eluate had a mAb Her2 concentration of 7.61 g/l with 98.8% purity. The immunoglobulin in aggregated form was produced/obtained by heating of the mAb Her2 solution to 37° C. for 3 days. The solution contained after the heat treatment 99.0% of the immunoglobulin in monomeric form and 1.0% of the immunoglobulin in aggregated form without considering low molecular weight substances present in the heat treated sample. The conditioned protein A eluate had been virus inactivated and filtered through a 0.2 μm pore size filter prior to the experiments. After dilution to a protein concentration of 1.03 mg/ml, pH and conductivity adjustment, the solution had been applied to the membrane cation exchange materials Sartobind™ S and C, respectively. The adjustment of conductivity was done by the addition of NaCl (5 mol/l). The results are shown in Tables 5 and 6.

TABLE 5 mAb Her2 immunoglobulin in monomeric and aggregated form (as area percentage of SEC chromatography) and yield with a Sartobind™ S membrane.

| Sample No. | Sample amount of mAb Her2 | Sample volume | mAb Her2 in monomeric form in flow-through | | | | mAb Her2 in aggregated form in flow-through | |
|---|---|---|---|---|---|---|---|---|
| | | | total concentration | area percentage | amount | yield | area percentage | amount |
| 1 | 11.35 mg | 11 ml | 0.053 mg/ml | 40.4% | 0.23 mg | 0.02% | bdl | — |
| 2 | 11.35 mg | 11 ml | 0.600 mg/ml | 99.2% | 6.47 mg | 57.0% | bdl | — |
| 3 | 11.35 mg | 11 ml | 0.908 mg/ml | 99.8% | 9.86 mg | 86.9% | 0.02% | 0.002 mg |
| 4 | 11.35 mg | 11 ml | 0.977 mg/ml | 99.9% | 10.60 mg | 93.4% | 0.03% | 0.003 mg |
| 5 | 11.35 mg | 11 ml | 0.999 mg/ml | 99.8% | 10.83 mg | 95.4% | bdl | — |
| 6 | 11.35 mg | 11 ml | 1.013 mg/ml | 99.9% | 10.99 mg | 96.8% | bdl | — |
| 7 | 11.35 mg | 11 ml | 1.019 mg/ml | 99.8% | 10.04 mg | 88.5% | 0.05% | 0.006 mg |
| 8 | 11.35 mg | 11 ml | 1.023 mg/ml | 99.9% | 11.10 mg | 97.8% | 0.08% | 0.009 mg |
| 9 | 11.35 mg | 11 ml | 1.025 mg/ml | 99.8% | 11.12 mg | 98.0% | 0.14% | 0.016 mg |
| 10 | 11.35 mg | 11 ml | 1.024 mg/ml | 99.8% | 11.11 mg | 97.9% | 0.17% | 0.019 mg |
| 11 | 11.35 mg | 11 ml | 1.025 mg/ml | 99.7% | 11.11 mg | 97.9% | 0.18% | 0.020 mg |
| 12 | 11.35 mg | 11 ml | 1.027 mg/ml | 99.7% | 11.13 mg | 98.1% | 0.23% | 0.026 mg |
| 13 | 11.35 mg | 11 ml | 1.028 mg/ml | 99.7% | 11.13 mg | 98.1% | 0.24% | 0.027 mg |
| 14 | 11.35 mg | 11 ml | 1.028 mg/ml | 99.6% | 11.13 mg | 98.1% | 0.30% | 0.034 mg |
| 15 | 11.35 mg | 11 ml | 1.027 mg/ml | 99.6% | 11.30 mg | 99.6% | 0.32% | 0.036 mg |
| Average of samples 4 to 15 | 11.35 mg | 11 ml | 1.018 mg/ml | 99.8% | 10.97 mg | 96.7% | 0.14% | 0.016 mg | bdl = below detection limit
— = not determined

TABLE 6 mAb Her2 immunoglobulin in monomeric and aggregated form (as area percentage of SEC chromatography) and yield with a Sartobind™ C membrane.

| Sample No. | Sample amount of mAb Her2 | Sample volume | mAb Her2 in monomeric form in flow-through | | | | mAb Her2 in aggregated form in flow-through | |
|---|---|---|---|---|---|---|---|---|
| | | | total concentration | area percentage | amount | yield | area percentage | amount |
| 1 | 11.35 mg | 11 ml | 0.082 mg/ml | 74.8% | 0.67 mg | 5.9% | bdl | — |
| 2 | 11.35 mg | 11 ml | 0.656 mg/ml | 99.1% | 7.07 mg | 62.3% | bdl | — |
| 3 | 11.35 mg | 11 ml | 0.861 mg/ml | 99.7% | 9.32 mg | 82.1% | bdl | — |
| 4 | 11.35 mg | 11 ml | 0.929 mg/ml | 99.7% | 10.06 mg | 88.6% | 0.04% | 0.004 mg |
| 5 | 11.35 mg | 11 ml | 0.965 mg/ml | 99.7% | 10.45 mg | 92.1% | 0.09% | 0.01 mg |
| 6 | 11.35 mg | 11 ml | 0.992 mg/ml | 99.7% | 10.47 mg | 92.2% | 0.15% | 0.015 mg |
| 7 | 11.35 mg | 11 ml | 1.004 mg/ml | 99.8% | 10.88 mg | 95.9% | 0.14% | 0.015 mg |
| 8 | 11.35 mg | 11 ml | 1.014 mg/ml | 99.7% | 10.98 mg | 96.7% | 0.24% | 0.027 mg |
| 9 | 11.35 mg | 11 ml | 1.015 mg/ml | 99.7% | 10.99 mg | 96.8% | 0.29% | 0.032 mg |
| 10 | 11.35 mg | 11 ml | 1.017 mg/ml | 99.6% | 11.00 mg | 96.9% | 0.36% | 0.04 mg |
| 11 | 11.35 mg | 11 ml | 1.019 mg/ml | 99.6% | 11.03 mg | 97.2% | 0.43% | 0.047 mg |
| 12 | 11.35 mg | 11 ml | 1.021 mg/ml | 99.5% | 11.04 mg | 97.3% | 0.41% | 0.046 mg |
| 13 | 11.35 mg | 11 ml | 1.022 mg/ml | 99.5% | 11.05 mg | 97.4% | 0.42% | 0.047 mg |
| 14 | 11.35 mg | 11 ml | 1.024 mg/ml | 99.5% | 11.07 mg | 97.5% | 0.51% | 0.055 mg |
| 15 | 11.35 mg | 11 ml | 1.024 mg/ml | 99.5% | 11.07 mg | 97.5% | 0.47% | 0.051 mg |
| Average of samples 4 to 15 | 11.35 mg | 11 ml | 1.0 mg/ml | 99.6% | 10.84 mg | 95.5% | 0.30% | 0.032 mg | bdl = below detection limit
— = not determined

Figure 4:
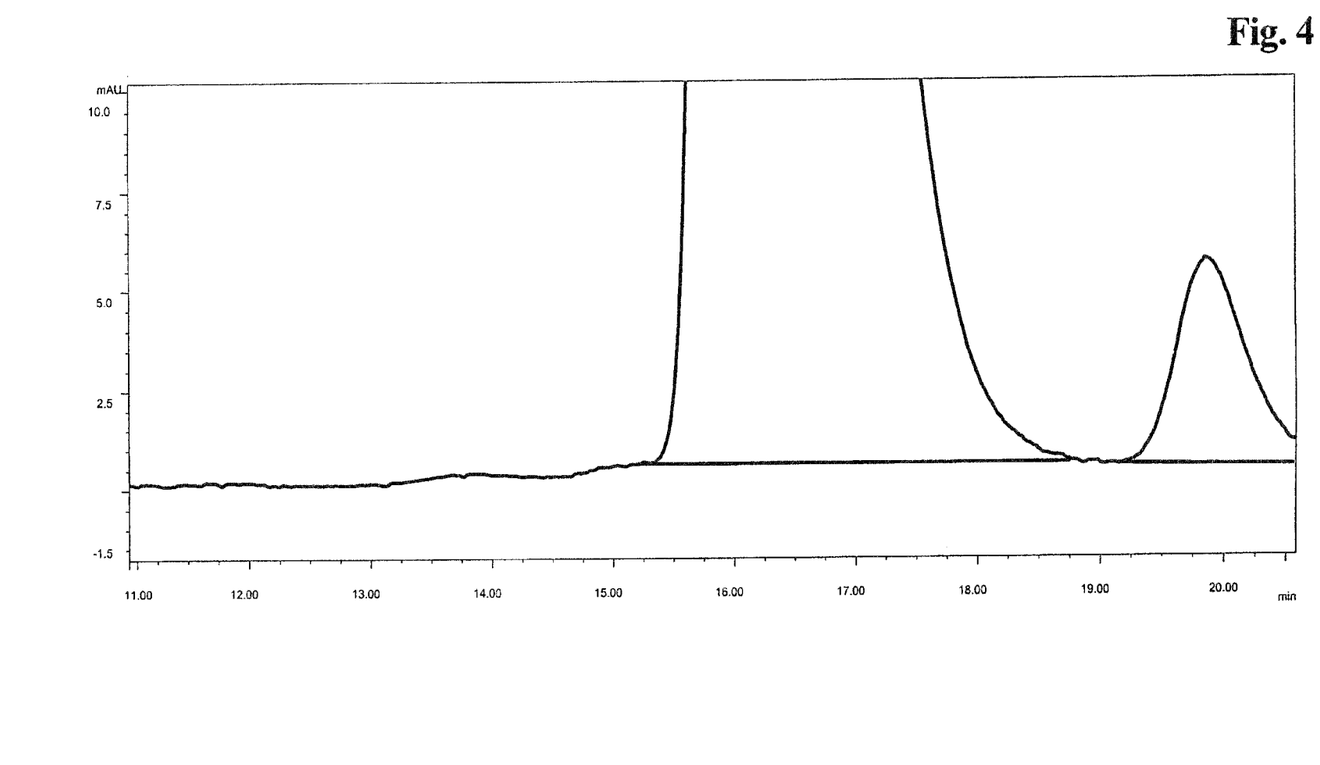
FIG. 4: SEC analysis of fraction 4 of the flow-through of a Sartobind™ C membrane process of sample material containing of mAb Her2.

An exemplary size exclusion chromatography (SEC) analysis of fraction 4 of the flow-through of a Sartobind™ C membrane is shown in FIG. 4.

It can be summarized from the above that the sum of pH value and conductivity in mS/cm is preferably in the range from 9 to 18, more preferably in the range from 10 to 15.

Example 4

Analysis of Protein A, DNA and HCP Content.

The fractions obtained in Example 2 have been analyzed for protein A-, DNA-, and HCP-content. The results are given in Tables 7 and 8.

The protein A-content in the solution prior to the application to the Sartobind™ S membrane was 2.6 ng/ml, the DNA-content was <0.3 pg/mg, and the host cell protein (HCP)-content was 1791 ng/mg.

TABLE 7

Protein A-, DNA-, and HCP-content of fractions containing mAb IL13 immunoglobulin obtained with a Sartobind ™ S membrane.

| Sample No. | Sample volume [ml] | Protein concentration [mg/ml] | protein A [ng/mg] | DNA [pg/mg] | HCP [ng/mg] |
|---|---|---|---|---|---|
| 1 | 11 | 0.029 | <4.1 | <138 | 28 |
| 2 | 11 | 0.513 | 0.5 | <0.8 | <118 |
| 3 | 11 | 0.889 | <0.3 | <0.4 | <202 |
| 4 | 11 | 0.935 | 0.7 | <0.4 | 255 |
| 5 | 11 | 0.939 | — | <0.4 | — |
| 6 | 11 | 0.943 | — | <0.4 | — |

— = not determined

The protein A-content in the solution prior to the application to the Sartobind™ C membrane was 3.0 ng/ml, the DNA-content was <0.4 pg/mg, and the host cell protein (HCP)-content was 5250 ng/mg.

TABLE 8

Protein A-, DNA-, and HCP-content of fractions containing mAb IL13 immunoglobulin obtained with a Sartobind ™ C membrane.

| Sample No. | Sample volume [ml] | Protein concentration [mg/ml] | protein A [ng/mg] | DNA [pg/mg] | HCP [ng/mg] |
|---|---|---|---|---|---|
| 1 | 11 | 0.033 | <4.2 | <13.3 | 155 |
| 2 | 11 | 0.559 | <0.2 | <0.7 | 1036 |
| 3 | 11 | 0.873 | 0.3 | <0.5 | 989 |
| 4 | 11 | 0.933 | 0.7 | <0.4 | 1366 |
| 5 | 11 | 0.959 | n. b. | n. b. | n. b. |
| 6 | 11 | 0.979 | n. b. | n. b. | n. b. |

The invention claimed is:

1. A method for obtaining an immunoglobulin in monomeric form from a solution comprising the immunoglobulin in monomeric and in aggregated form, characterized in that said method comprises the following step:
   a) applying an aqueous, buffered solution comprising said immunoglobulin in monomeric and in aggregated form to a cation exchange material under conditions whereby said immunoglobulin in monomeric form does not bind to said cation exchange material, and recovering said immunoglobulin in monomeric form from said solution after the contact with said cation exchange material,
   wherein said aggregated form is an immunoglobulin molecule associated covalently or non-covalently with at least one additional immunoglobulin molecule, and wherein said cation exchange material is the sole chromatography material in step a).

2. The method according to claim 1, characterized in that said step a) is a chromatographic step operated in flow-through mode comprising applying an aqueous, buffered solution comprising said immunoglobulin in monomeric and in aggregated form to a cation exchange material under conditions whereby said immunoglobulin in monomeric form does not bind to said cation exchange material, and recovering said immunoglobulin in monomeric form from said solution after the contact with said cation exchange material.

3. The method according to claim 1, characterized in that said method comprises prior to step a) the following step:
   b) applying an aqueous, buffered solution comprising said immunoglobulin in monomeric and in aggregated form to an anion exchange material under conditions whereby said immunoglobulin does not bind to said anion exchange material, and recovering said immunoglobulin in monomeric and in aggregated form from said solution after the contact with said anion exchange material.

4. The method according to claim 3, characterized in that said step b) is a chromatographic step operated in flow through-mode comprising applying an aqueous, buffered solution comprising said immunoglobulin in monomeric and in aggregated form to an anion exchange material under conditions whereby said immunoglobulin does not bind to said anion exchange material, and recovering said immunoglobulin in monomeric and in aggregated form from said solution after the contact with said anion exchange material.

5. The method according to claim 1, characterized in that said method comprises after step a) the following step:
   c) applying an aqueous, buffered solution comprising said immunoglobulin in monomeric form to an anion exchange material under conditions whereby said immunoglobulin does not bind to said anion exchange material, and recovering said immunoglobulin in monomeric form from said solution after the contact with said anion exchange material.

6. The method according to claim 5, characterized in that said step c) is a chromatographic step operated in flow-through mode comprising applying an aqueous, buffered solution comprising said immunoglobulin in monomeric form to an anion exchange material under conditions whereby said immunoglobulin does not bind to said anion exchange material, and recovering said immunoglobulin in monomeric form from said solution after the contact with said anion exchange material.

7. The method according to claim 1, characterized in that said method comprises either prior to step a) or prior to step b) the following further step:
   d) applying an aqueous, buffered solution comprising said immunoglobulin in monomeric and in aggregated form to an affinity column under conditions whereby said immunoglobulin binds to said affinity column, and recovering said immunoglobulin in monomeric and in aggregated form from said affinity column.

8. The method according to claim 7, characterized in that said step d) is a chromatographic step operated in bind-and-elute mode comprising applying an aqueous, buffered solution comprising said immunoglobulin in monomeric and in aggregated form to an affinity column under conditions whereby said immunoglobulin binds to said affinity column, and recovering said immunoglobulin in monomeric and in aggregated form from said affinity column.

9. The method according to claim 1, characterized in that in said step a) the cation exchange material is a membrane cation exchange material.

10. The method according to claim 9, characterized in that said membrane cation exchange material is a strong or weak cation exchange material.

11. The method according to claim 9, characterized in that said membrane cation exchange material is a polyethersulfone based membrane or a regenerated cellulose based membrane modified with sulfonic acid groups or carboxymethyl groups.

12. The method according to claim 1, characterized in that said aqueous, buffered solution of step a) has a pH value of from pH 5 to pH 8.

13. The method according to claim 1, characterized in that said aqueous, buffered solution of step a) has a conductivity of from 1.0 to 15.0 mS/cm.

14. The method according to claim 13, characterized in that said aqueous, buffered solution of step a) has a conductivity of from 4.0 to 10.0 mS/cm.

15. The method according to claim 1, characterized in that said recovering said immunoglobulin in monomeric form from the flow-through is by a method selected from precipitation, salting out, ultrafiltration, diafiltration, lyophilization, affinity chromatography, or solvent volume reduction to obtain a concentrated solution.

16. The method according to claim 15, characterized in that said recovering is by ultrafiltration, lyophilization, or solvent volume reduction.

17. The method according to claim 1, characterized in that of said immunoglobulin obtained from the flow-through of the membrane cation exchange material at least 95% of the immunoglobulin is in monomeric form.

18. The method according to claim 1, characterized in that at least 90% of the immunoglobulin in monomeric form does not bind to the cation exchange material.

19. The method according to claim 1, characterized in that said aqueous, buffered solution is a solution comprising phosphoric acid or salts thereof citric acid or salts thereof, or histidine or salts thereof.

20. The method according to claim 1, characterized in that said aqueous, buffered solution comprises sodium chloride or potassium chloride.

21. The method according to claim 1, characterized in that said chromatographic step is a column chromatography or a cassette chromatography.

22. The method according to claim 1, characterized in that the sum of pH value and conductivity in mS/cm of the aqueous, buffered solution in step a) is in the range of from 9 to 18.

23. The method according to claim 22, characterized in that said sum is in the range of from 10 to 15.

24. The method according to claim 9, wherein the membrane cation exchange material is a polyethersulfone-based membrane or a regenerated cellulose-based membrane modified with sulfonic acid groups or carboxymethyl groups.

* * * * *